United States Patent
Takashino et al.

(10) Patent No.: US 10,058,373 B2
(45) Date of Patent: Aug. 28, 2018

(54) TREATMENT INSTRUMENT AND TREATMENT SYSTEM

(71) Applicant: OLYMPUS CORPORATION, Hachioji-shi, Tokyo (JP)

(72) Inventors: Tomoyuki Takashino, Fuchu (JP); Hiroaki Ichikawa, Yokohama (JP); Yusuke Takei, Hino (JP); Kazuhiro Tanaka, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/409,961

(22) Filed: Jan. 19, 2017

(65) Prior Publication Data

US 2017/0128121 A1  May 11, 2017

Related U.S. Application Data

(63) Continuation of application No. PCT/JP2015/079960, filed on Oct. 23, 2015.

(30) Foreign Application Priority Data

Nov. 11, 2014  (JP) ................. 2014-229014

(51) Int. Cl.
  *A61B 18/14*  (2006.01)
  *A61B 18/08*  (2006.01)
  (Continued)

(52) U.S. Cl.
  CPC ........ *A61B 18/085* (2013.01); *A61B 17/0644* (2013.01); *A61B 17/0682* (2013.01);
  (Continued)

(58) Field of Classification Search
  CPC ............ A61B 17/0644; A61B 17/0682; A61B 17/07207; A61B 18/085; A61B 18/10;
  (Continued)

(56) References Cited

U.S. PATENT DOCUMENTS 5,507,773 A * 4/1996 Huitema .......... A61B 17/07207
                                                        600/564
7,329,257 B2   2/2008 Kanehira et al.
(Continued)

FOREIGN PATENT DOCUMENTS

EP  3 034 023 A1  6/2016
EP  3 087 941 A1  11/2016
(Continued)

OTHER PUBLICATIONS

Jan. 19, 2016 International Search Report issued in International Patent Application No. PCT/JP2015/079960.
(Continued)

*Primary Examiner* — Michael Peffley
*Assistant Examiner* — Amanda Zink
(74) *Attorney, Agent, or Firm* — Oliff PLC

(57) ABSTRACT

A treatment instrument includes a treatment body that includes a treatment surface provided in the first clamp surface, the treatment surface protruding toward the second clamp surface in response to the supply of heat energy and increasing pressure on the living tissue to treat the living tissue in cooperation with the action of the heat energy.

25 Claims, 12 Drawing Sheets

(51) Int. Cl.
*A61B 17/068* (2006.01)
*A61B 17/064* (2006.01)
*A61B 17/072* (2006.01)
*A61B 18/10* (2006.01)
*A61B 17/00* (2006.01)
*A61B 18/00* (2006.01)

(52) U.S. Cl.
CPC ........ *A61B 17/07207* (2013.01); *A61B 18/10* (2013.01); *A61B 2017/00004* (2013.01); *A61B 2017/07228* (2013.01); *A61B 2017/07257* (2013.01); *A61B 2017/07285* (2013.01); *A61B 2018/0063* (2013.01); *A61B 2018/0094* (2013.01); *A61B 2018/00601* (2013.01); *A61B 2018/00714* (2013.01)

(58) Field of Classification Search
CPC  A61B 2017/00004; A61B 2017/07228; A61B 2017/07257; A61B 2017/07285; A61B 2018/00601; A61B 2018/0063; A61B 2018/00714; A61B 2018/0094
See application file for complete search history.

(56) References Cited

U.S. PATENT DOCUMENTS

| | | | |
|---|---|---|---|
| 2003/0181910 A1* | 9/2003 | Dycus | A61B 18/1445 606/51 |
| 2003/0187429 A1* | 10/2003 | Karasawa | A61B 18/085 606/28 |
| 2003/0220637 A1* | 11/2003 | Truckai | A61B 18/1442 606/28 |
| 2005/0288747 A1 | 12/2005 | Aoki et al. | |
| 2013/0018372 A1 | 1/2013 | Sims et al. | |
| 2014/0128867 A1 | 5/2014 | Collings et al. | |
| 2017/0042602 A1 | 2/2017 | Takashino et al. | |

FOREIGN PATENT DOCUMENTS

| | | |
|---|---|---|
| EP | 3 189 804 A1 | 7/2017 |
| JP | S62-233153 A | 10/1987 |
| JP | H06-296577 A | 10/1994 |
| JP | 2004-000460 A | 1/2004 |
| JP | 2005-348820 A | 12/2005 |
| WO | 2008/109695 A2 | 9/2008 |
| WO | 2015/122351 A1 | 8/2015 |

OTHER PUBLICATIONS

Jun. 12, 2018 Extended European Search Report issued in European Patent Application No. 15859711.2.

\* cited by examiner

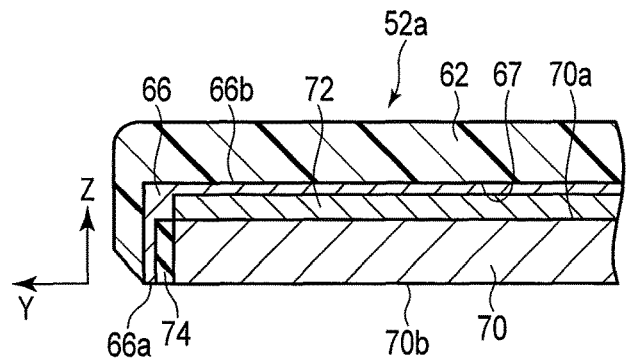
F I G. 4A
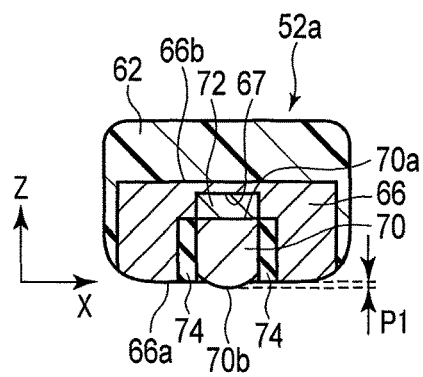
F I G. 4B
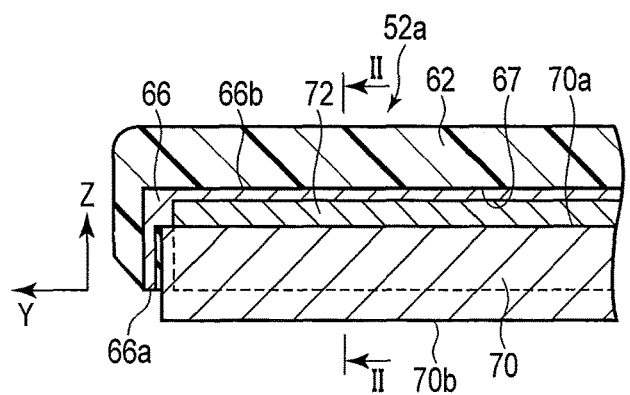
F I G. 5A

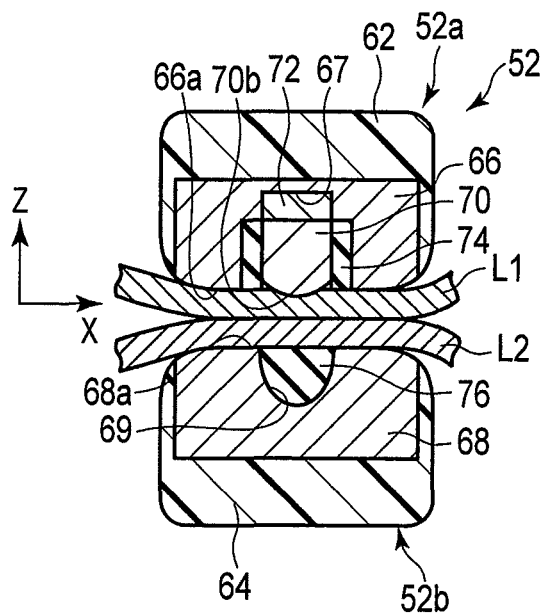
F I G. 7A
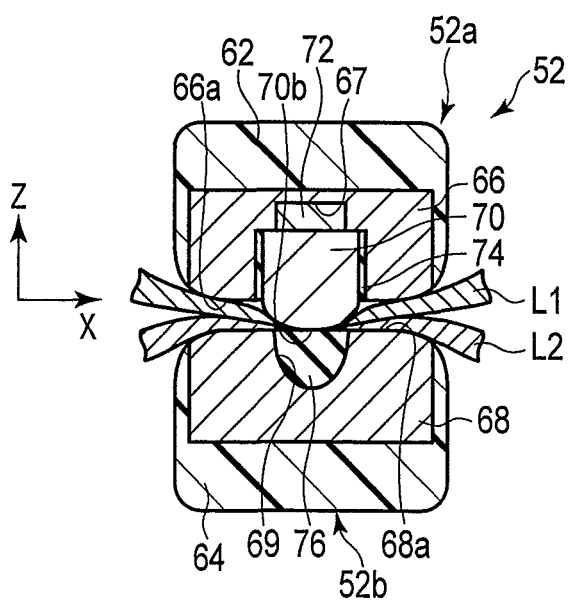
F I G. 7B

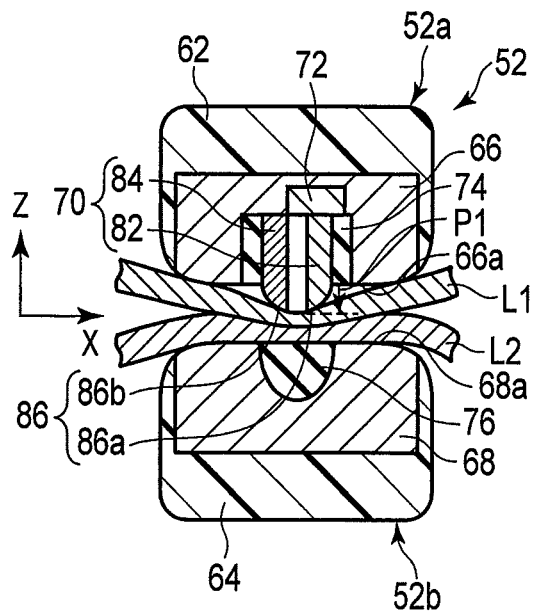
F I G. 8A
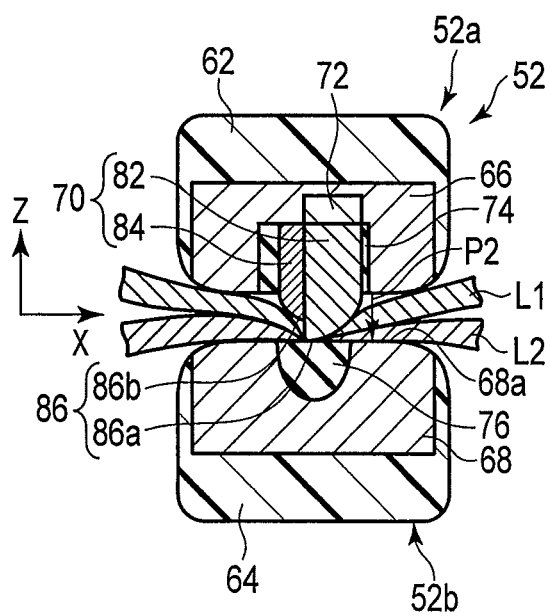
F I G. 8B

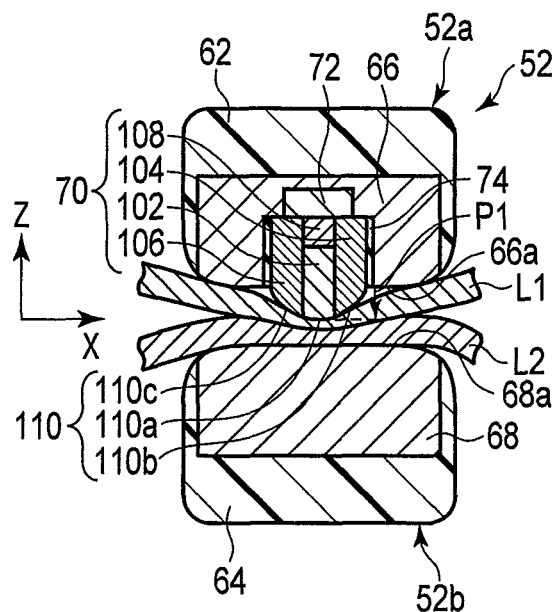
F I G. 10A
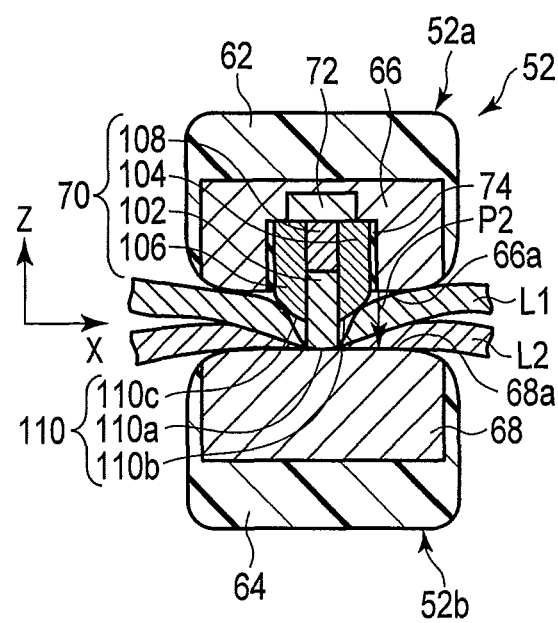
F I G. 10B

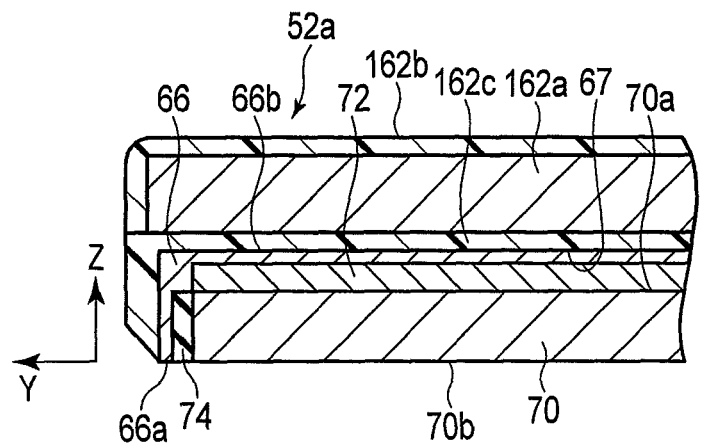
F I G. 11A
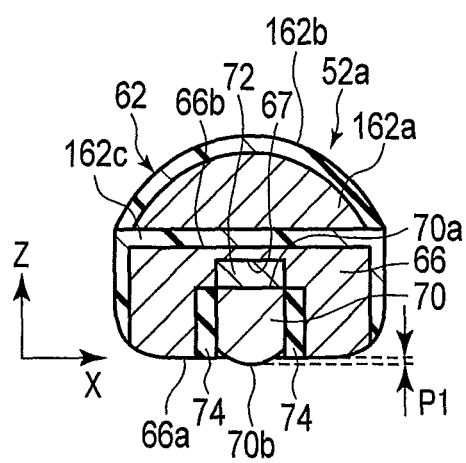
F I G. 11B

TREATMENT INSTRUMENT AND TREATMENT SYSTEM

CROSS-REFERENCE TO RELATED APPLICATIONS

This application is a Continuation Application of PCT Application No. PCT/JP2015/079960, filed Oct. 23, 2015 and based upon and claiming the benefit of priority from prior Japanese Patent Application No. 2014-229014, filed Nov. 11, 2014, the entire contents of all of which are incorporated herein by reference.

BACKGROUND OF THE INVENTION

1. Field of the Invention

The present invention relates to a treatment instrument and a treatment system to treat a living tissue by use of heat energy.

2. Description of the Related Art

For example, the specification of U.S. Pat. No. 7,329,257 discloses a treatment instrument to treat a living tissue clamped between a pair of clamp surfaces by use of energy. This treatment instrument has one of the clamp surfaces protruding toward the other clamp surface, and has the protruding portion thinly formed in the width direction. Thus, this treatment instrument applies heat energy to the treatment target living tissue while linearly applying pressure to the living tissue so that the living tissue is easily cut open.

BRIEF SUMMARY OF THE INVENTION

According to one aspect of the present invention, a treatment instrument includes: a first clamp portion including a first clamp surface; a second clamp portion including a second clamp surface which faces the first clamp surface and which cooperates with the first clamp surface to clamp a living tissue; and a treatment body that is provided in the first clamp portion and that includes a treatment surface, the treatment surface protruding as much as a first protrusion amount from the first clamp surface when the supply of heat energy is stopped and protruding a second protrusion amount protruding more than the first protrusion amount from the first clamp surface in response to the supply of the heat energy, in a state where the living tissue is clamped between the first and second clamp surfaces, the treatment surface increasing pressure on the living tissue when reaching the second protrusion amount from the first protrusion amount, to treat the living tissue in cooperation with the action of the heat energy.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4A is a schematic longitudinal sectional view taken along the I-I line in FIG. 3 in a state where the supply of heat energy to a treatment body from a heating element in the first treatment piece of the treatment portion of the treatment instrument of the treatment system according to the first embodiment is stopped;

FIG. 4B is a schematic cross sectional view taken along the II-II line in FIG. 3 showing the first treatment piece of the treatment portion of the treatment instrument of the treatment system according to the first embodiment;

FIG. 5A is a schematic longitudinal sectional view taken along the I-I line in FIG. 3 and FIG. 5B in a state where heat energy is supplied to the treatment body from the heating element in the first treatment piece of the treatment portion of the treatment instrument of the treatment system according to the first embodiment;

FIG. 7A is a schematic cross sectional view showing a state where living tissues are clamped between the first treatment piece shown in FIG. 4B and the second treatment piece shown in FIG. 6B;

FIG. 7B is a schematic cross sectional view showing a state where the living tissues clamped between the first treatment piece and the second treatment piece shown in FIG. 6B are cut open by the treatment body which is thermally expanded by heat transmission from the heating element in the first treatment piece shown in FIG. 5B;

FIG. 8A is a schematic cross sectional view showing the treatment portion of the treatment instrument of the treatment system according to a first modification of the first embodiment, and showing a state where the living tissues are clamped between a protruding body and a thermal expansion member of the treatment body of the first treatment piece that are adjacent to each other, and a second clamp surface of the second treatment piece;

FIG. 8B is a schematic cross sectional view showing the treatment portion of the treatment instrument of the treatment system according to the first modification of the first embodiment, and showing a state where the thermal expansion member is expanded by the application of heat energy between the protruding body and the thermal expansion member of the treatment body of the first treatment piece that are adjacent to each other, and the living tissues clamped between the second clamp surface of the second treatment piece and the thermal expansion member are cut open by the thermal expansion member;

FIG. 10A is a schematic cross sectional view showing the treatment portion of the treatment instrument of the treatment system according to a third modification of the first embodiment, and showing a state where the living tissues are clamped between a movable body provided, between a deformable body and the protruding body, in the deformable body which is disposed between the pair of protruding bodies and the protruding body of the treatment body of the first treatment piece and which is deformed by the application of heat, and the second clamp surface of the second treatment piece;

FIG. 10B is a schematic cross sectional view showing the treatment portion of the treatment instrument of the treatment system according to the third modification of the first embodiment, and showing a state where heat energy is applied to the deformable body of the treatment body of the first treatment piece to deform the deformable body, and the living tissues clamped between the second clamp surface of the second treatment piece and the movable body are cut open by the movable body provided in the deformable body;

FIG. 11A is a schematic longitudinal sectional view taken along the I-I line in FIG. 3 in a state where the supply of heat energy to the treatment body from the heating element in the first treatment piece of the treatment portion of the treatment instrument of the treatment system according to a fourth modification of the first embodiment is stopped;

FIG. 11B is a schematic cross sectional view taken along the II-II line in FIG. 3 showing the first treatment piece of the treatment portion of the treatment instrument of the treatment system according to the fourth modification of the first embodiment;

DETAILED DESCRIPTION OF THE INVENTION

Hereinafter, embodiments of this invention will be described with reference to the drawings.

Initially, the first embodiment is described with reference to FIG. 1 to FIG. 7B.

Figure 1:
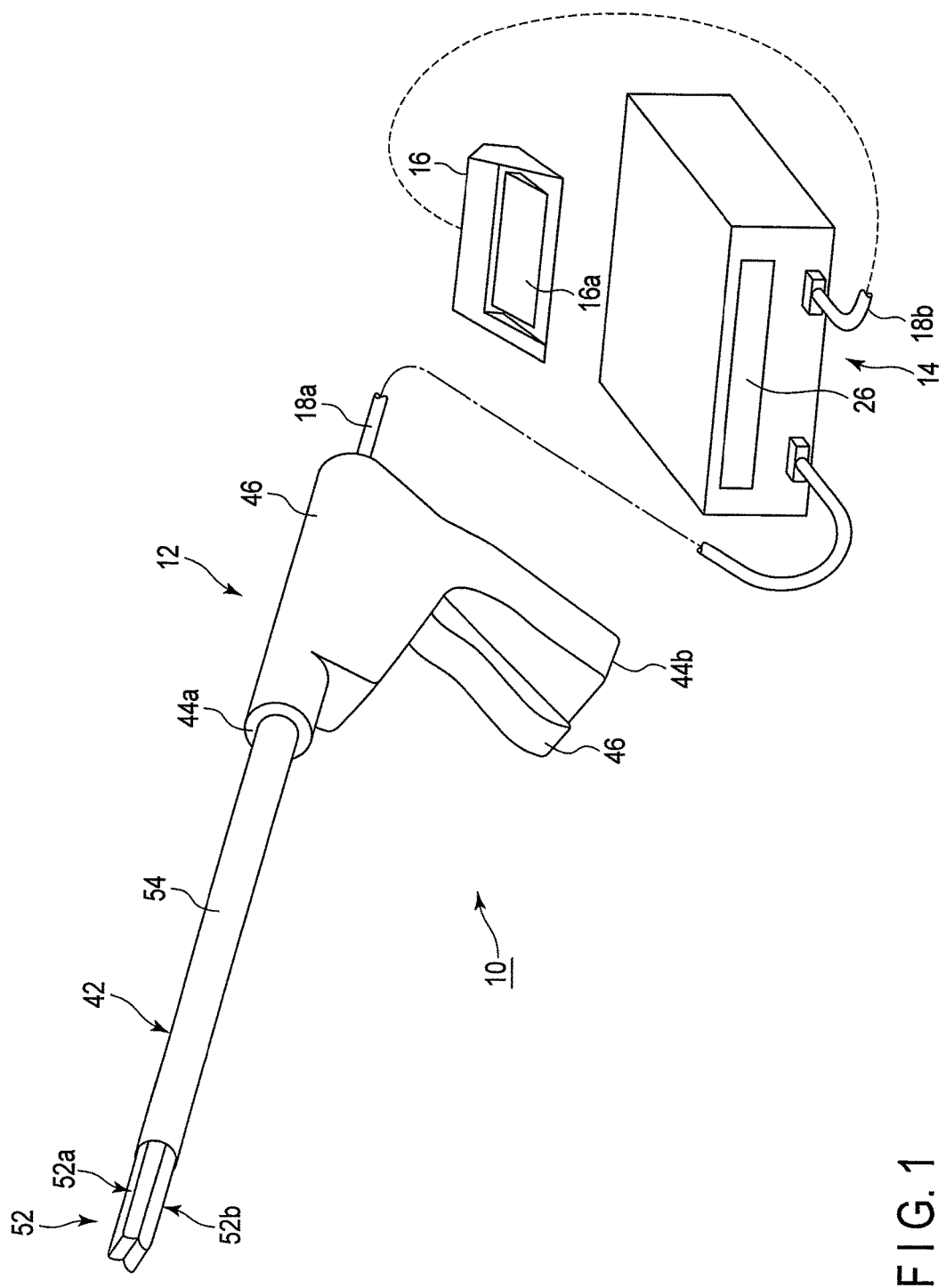
FIG. 1 is a schematic diagram showing a treatment system according to a first embodiment.
Figure 2:
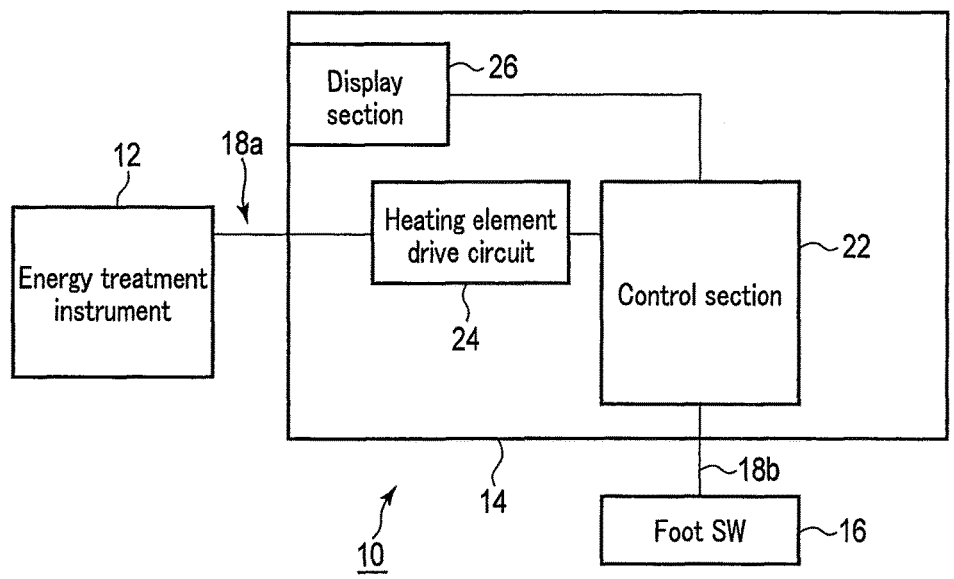
FIG. 2 is a schematic block diagram showing the treatment system according to the first embodiment.

As shown in FIG. 1 to FIG. 2, a treatment system 10 according to this embodiment includes a treatment instrument (energy treatment instrument) 12, and a controller 14 which applies energy to the treatment instrument 12. The controller 14 controls the temperature of a later-described heating element 72 of the treatment instrument 12 to a suitable temperature.

A foot switch 16 having a pedal 16a to switch on and off energy to be applied to the treatment instrument 12 is connected to the controller 14. The treatment instrument 12 and the controller 14 are electrically connected to each other by a first cable 18a, and the controller 14 and the foot switch 16 are electrically connected to each other by a second cable 18b. The foot switch 16 can input signals to the controller 14, for example, by the operation of the pedal 16a, and the controller 14 can control energy to be applied to the treatment instrument 12 on the basis of, for example, the operation of the pedal 16a of the foot switch 16.

A surgeon operates the pedal 16a of the foot switch 16 to switch on and off the supply of energy to the treatment instrument 12 from the controller 14. When the pedal 16a is pressed, the later-described heating element 72 is heated to transmit heat to a treatment body (thermal expansion member) 70 and a first clamp portion 66. When the pedal 16a is released, the supply of energy to the heating element 72 is stopped.

It should be understood that an unshown hand switch may be used instead of or together with the foot switch 16.

As shown in FIG. 2, the controller 14 includes a control section 22 including a CPU and others, a heating element drive circuit (energy output circuit) 24 as an energy source, and a display section 26. The heating element drive circuit 24 and the display section 26 are controlled by the control section 22. The display section 26 is used to display the state of the controller 14 and to perform various settings. For example, the temperature of the later-described heating element (energy output portion) 72 may be displayed on the display section 26.

If the pedal 16a of the foot switch 16 is pressed in a state where the foot switch 16 is electrically connected to the control section 22 of the controller 14, energy is output to the later-described heating element 72 from the heating element drive circuit 24. In this instance, the control section 22 can adjust the energy which is output to the heating element 72 from the heating element drive circuit 24 to adjust the temperature of the heating element 72 (the rising temperature and the maximum temperature per unit time).

As shown in FIG. 1, the treatment instrument 12 includes an insertion portion 42 and an operation portion 44. The insertion portion 42 includes a treatment portion 52 to treat living tissues L1 and L2, and a shaft 54. The proximal end of the shaft 54 is coupled to one end 44a of the operation portion 44. The treatment portion 52 is provided at the distal end of the shaft 54. The treatment portion 52 includes a first treatment piece 52a and a second treatment piece 52b.

The first and second treatment pieces 52a and 52b are opened and closed by a known mechanism by the operation of an open/close lever (open/close knob) 46 of the operation portion 44. If the open/close lever 46 is operated to come closer to the other end 44b of the operation portion 44, at least one of the first and second treatment pieces 52a and 52b is moved, for example, by known means such as a wire or a rod disposed inside the insertion portion 42, and the first and second treatment pieces 52a and 52b come closer to each other and close. If the open/close lever 46 is operated to come away from the other end 44b of the operation portion 44, at least one of the first and second treatment pieces 52a and 52b is moved by the known means, and the first and second treatment pieces 52a and 52b come away from each other and open. Only one of the first and second treatment pieces 52a and 52b may be movable by the operation of the open/close lever 46 of the operation portion 44, or both of them may be movable. That is, the first and second treatment pieces 52a and 52b are relatively openable and closable.

The treatment portion 52 includes a pair of jaws (first and second jaws) 62 and 64, the first clamp portion 66 having a first clamp surface 66a, a second clamp portion 68 having a second clamp surface 68a, and the treatment body 70 provided in the first clamp surface 66a. The second clamp surface 68a of the second clamp portion 68 faces the first clamp surface 66a, and cooperates with the first clamp surface 66a to clamp the living tissues L1 and L2. The heating element (energy output portion) 72 is provided inside the first clamp portion 66 or in a back surface 66b thereof. That is, the treatment portion 52 includes the first jaw 62 in which the first clamp portion 66 is provided and which can bring the first clamp surface 66a and the second clamp surface 68a closer to and away from each other. The treatment portion 52 includes the second jaw 64 in which the second clamp portion 68 is provided and which can bring the first clamp surface 66a and the second clamp surface 68a closer to and away from each other.

In this embodiment, the heating element 72 is formed as a heater which is heated when energy is input thereto. The heating element 72 is electrically connected to the heating element drive circuit 24 of the controller 14 via the insertion portion 42 and the operation portion 44. Thus, energy is output to the heating element 72 from the heating element drive circuit 24 by the operation of the pedal 16a of the foot switch 16 to heat the heating element 72. When the heating element 72 is heated, it is preferable that the temperature of the clamp surface 66a of the first clamp portion 66 and the temperature of a treatment surface 70b of the treatment body 70 can be respectively raised within several seconds between room temperature and a temperature of, for example, about 150° C. to 300° C.

The first treatment piece 52a is formed by the first jaw 62, the first clamp portion 66, the treatment body 70, and the heating element 72. The second treatment piece 52b is formed by the second jaw 64 and the second clamp portion 68.

For example, ceramics, resin materials having heat resistance and electric insulation, and insulated metallic materials are suitably used for the first and second jaws 62 and 64. It is also preferable to use materials having heat resistance to the first and second jaws 62 and 64.

The first clamp portion 66 is provided in the first jaw 62. The back surface 66b of the first clamp portion 66 opposite to the first clamp surface 66a is supported by the first jaw 62 or fixed to the first jaw 62.

As shown in FIG. 3 to FIG. 5B, in this embodiment, a longitudinal direction through a distal end Y1 and a proximal end Y2 of the first clamp portion 66 is defined as a Y-direction, a width direction that intersects at right angles with the longitudinal direction Y is defined as an X-direction, and a height direction relative to the first clamp surface 66a of the first clamp portion 66 (an open/close direction relative to the second clamp portion 68) is defined as a Z-direction. That is, the longitudinal direction Y of the first clamp portion 66 is defined by the distal end Y1 and the proximal end Y2 of the first clamp portion 66. The width direction X of the first clamp portion 66 is defined by a pair of edges X1 and X2 of the first clamp portion 66. A line that connects the centers of the pair of edges X1 and X2 along the longitudinal direction Y is a central line C.

The first clamp portion 66 is formed into a substantially rectangular flat shape which is long in a direction along the longitudinal direction Y of the insertion portion 42 and which is smaller in the width direction X that intersects at right angles with the longitudinal direction Y than in the longitudinal direction Y. The first clamp portion 66 is preferably made of a metallic material having satisfactory heat resistance. For example, an Fe—Ni 36% alloy material (thermal expansion coefficient: $0.8 \times E^{-6}[1/K]$) is used for the first clamp portion 66. That is, it is preferable to use a material having a low thermal expansion coefficient for the first clamp portion 66.

Heat (heat energy) from the heating element 72 is transmitted to the first clamp portion 66. Therefore, if the heating element 72 is heated by the supply of energy, heat can be transmitted to the first clamp surface 66a, and the temperature of the first clamp surface 66a rises.

Figure 3:
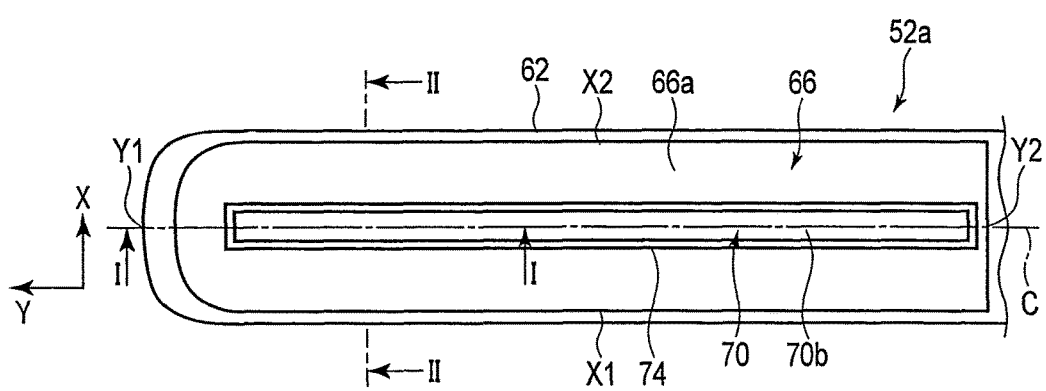
FIG. 3 is a schematic diagram showing a clamp surface in a first clamp portion of a first treatment piece of a treatment portion of a treatment instrument of the treatment system according to the first embodiment.
Figure 5B:
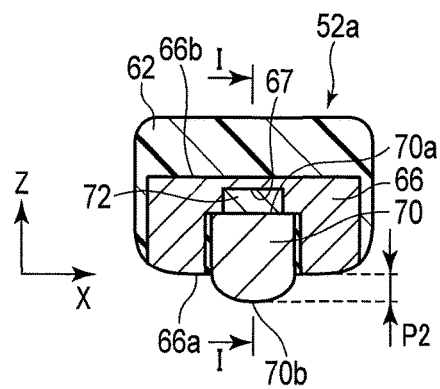
FIG. 5B is a schematic cross sectional view taken along the II-II line in FIG. 3 and FIG. 5A showing the first treatment piece of the treatment portion of the treatment instrument of the treatment system according to the first embodiment.

As shown in FIG. 3, FIG. 4B, and FIG. 5B, a depression 67 is formed in the first clamp surface 66a of the first clamp portion 66 substantially in the center (on the reference sign C in FIG. 3) in the width direction X from the first clamp surface 66a to the first jaw 62. Preferably, the depression 67 is formed with a suitable length along the longitudinal direction Y. Here, as shown in FIG. 3, the depression 67 is formed between the distal end Y1 and the proximal end Y2 of the first clamp portion 66. The heating element 72 is provided in the depression 67.

That is, in the first clamp portion 66, the heating element 72 is provided in the back surface 66b or at a position close to the back surface 66b.

At room temperature, the length of the treatment body 70 is slightly smaller than the length of the depression 67 along the longitudinal direction Y, and slightly smaller than the width of the depression 67 along the width direction X. A heating region of the heating element 72 is substantially the same as the length of the depression 67 along the longitudinal direction Y. Here, the heating element 72 is uniformly heated from its distal end to proximal end.

The treatment body 70 is provided in the depression 67. In other words, the heating element 72 is fixed to the treatment body 70. An elastically deformable buffer portion 74 having heat resistance is provided between the depression 67 and the treatment body 70. It is appropriate to use, for example, heat-resistant paper woven with ceramic fibers for the buffer portion 74. It is also preferable to use steel wool made of stainless steel for the buffer portion 74. Moreover, it is also appropriate to use an elastically deformable resin material such as silicone rubber if functions are ensured at a temperature of, for example, about 300° C.

The treatment body 70 includes a heat transmission surface 70a to which heat is transmitted (which receives heat) from the heating element 72, and the treatment surface (edge) 70b which is located opposite to the heat transmission surface 70a and which protrudes toward the clamp surface 68a of the second clamp portion 68 from the clamp surface 66a of the first clamp portion 66 to treat the living tissues L1 and L2. The treatment surface 70b of the treatment body 70 is extended along the longitudinal direction Y of the first clamp portion 66. The treatment surface 70b has a suitable length along the longitudinal direction Y of the first clamp portion 66, and has a width shorter than the length of the treatment surface 70b in the longitudinal direction Y and smaller than the width of the first clamp portion 66 in the width direction X that intersects at right angles with the longitudinal direction Y. The treatment surface 70b is formed into a blunt shape. It is therefore possible to minimize the trace of clamping that is left in the living tissues L1 and L2 in a state where the living tissues L1 and L2 are clamped between the clamp surfaces 66a and 68a of the first and second clamp portions 66 and 68.

For example, an aluminum alloy (thermal expansion coefficient: $23.1 \times E^{-6}[1/K]$) having satisfactory heat resistance is used for the treatment body 70 provided in the first clamp portion 66. That is, the thermal expansion coefficient of the treatment body 70 is about 20 times or 30 times higher than the thermal expansion coefficient of the first clamp portion 66. Thus, if the heating element 72 is heated, the temperature of the treatment surface 70b of the treatment body 70 rises, and the treatment body 70 expands as compared to the first clamp portion 66. That is, the treatment body 70 is made of a material which expands when heat energy of the heating element 72 is transmitted thereto.

When no energy is output to the treatment body 70 from the heating element 72, a first protrusion amount (initial protrusion amount) P1 of the treatment surface 70b of the treatment body 70 relative to the first clamp surface 66a of the first clamp portion 66 is preferably about 0 mm (flush with the treatment surface 70b) to 1 millimeter. The first protrusion amount P1 may be negative depending on the thermal expansion coefficient. That is, it is also appropriate that the treatment surface 70b of the treatment body 70 be retracted relative to the clamp surface 66a of the first clamp portion 66.

When energy is output to the treatment body 70 from the heating element 72 (i.e., heat is transmitted to the treatment body 70), a maximum protrusion amount (second protrusion amount) P2 of the treatment surface 70b of the treatment body 70 relative to the first clamp surface 66a of the first clamp portion 66 is preferably greater than the first protrusion amount P1 by, for example, about 1 millimeter to several millimeters. The second protrusion amount P2 is always positive, and the treatment surface 70b of the treatment body 70 is protruding from the first clamp surface 66a of the first clamp portion 66.

That is, the treatment surface 70b of the treatment body 70 is provided in the first clamp portion 66, and protrudes as much as the first protrusion amount P1 from the first clamp surface 66a when the supply of heat energy is stopped in a state where the living tissues L1 and L2 are clamped between the first and second clamp surfaces 66a and 68a. The treatment surface 70b of the treatment body 70 then has the second protrusion amount P2 which protrudes more than the first protrusion amount P1 from the first clamp surface 66a in response to the supply of heat energy. The treatment surface 70b of the treatment body 70 increases pressure on the living tissues L1 and L2 when reaching the second protrusion amount P2 from the first protrusion amount P1, to treat the living tissues L1 and L2 in cooperation with the action of the heat energy.

The second clamp portion 68 is provided in the second jaw 64. A back surface 68b of the second clamp portion 68 opposite to the clamp surface 68a is supported by the second jaw 64 or fixed to the second jaw 64. The second clamp portion 68 is preferably made of a metallic material. The second clamp portion 68 is made of, for example, copper.

The clamp surface 68a of the second clamp portion 68 faces the clamp surface 66a of the first clamp portion 66.

Figure 6A:
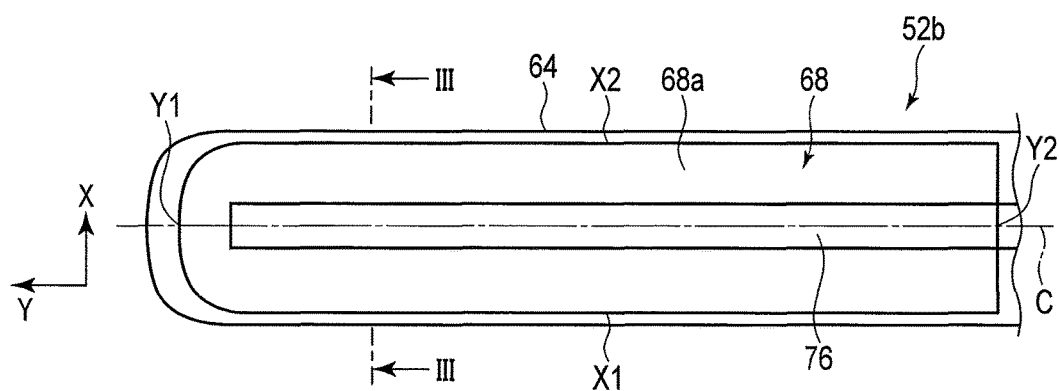
FIG. 6A is a schematic diagram showing a clamp surface in a second clamp portion of a second treatment piece of the treatment portion of the treatment instrument of the treatment system according to the first embodiment.
Figure 6B:
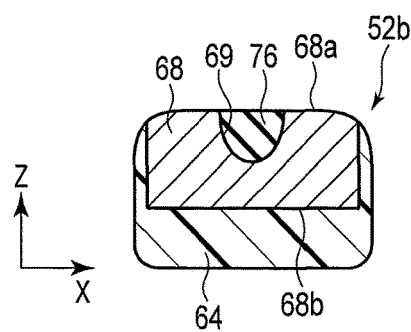
FIG. 6B is a schematic cross sectional view taken along the line in FIG. 6A showing the second treatment piece of the treatment portion of the treatment instrument of the treatment system according to the first embodiment.

A depression 69 is formed in the clamp surface 68a of the second clamp portion 68 substantially in the center in the width direction X from the clamp surface 68a to the second jaw 64. The depression 69 is preferably formed with a suitable length along the longitudinal direction Y. Here, as shown in FIG. 6A, the depression 69 is formed between the distal end and proximal end of the second clamp portion 68.

An elastic member 76 having heat resistance is provided in the depression 69. The elastic member 76 is formed to be substantially the same as or longer than the length of the facing treatment body 70 along the longitudinal direction Y. That is, the clamp surface 68a of the second clamp portion 68 includes the elastic member 76 which has heat resistance to the temperature of the treatment body 70 that is being supplied with heat energy and which receives the treatment surface 70b of the treatment body 70.

For example, heat-resistant paper that uses ceramic fibers can be used for the elastic member 76. The ceramic fibers have a high heat resistance of 100° C. or more, and can resist the temperature of the treatment surface 70b of the treatment body 70. The heat-resistant paper is formed by weaving into a paper form. This heat-resistant paper is soft like felt cloth, and elastic.

A material in which thin wires made of a metallic material are rounded like steel wool can be used for the elastic member 76 as a heat-resistant member. However, iron steel wool might be oxidized and catch fire when heated, and it is therefore preferable to use a stainless steel material.

The heating element drive circuit 24 of the controller 14 can control the surface temperature of the heating element 72 of the treatment instrument 12. Specifically, the controller 14 can control the temperature of the surface (living tissue holding surface) of the treatment body 70 when the heating element 72 is heated and this heat (heat energy) is transmitted to the treatment body 70. The heat (heat energy) can be then transmitted to the treatment target living tissues L1 and L2 through the treatment surface 70b of the treatment body 70.

The heating element drive circuit 24 of the controller 14 is controlled to apply energy to the heating element 72, for example, for several seconds (e.g., about 10 seconds at the maximum) to heat the heating element 72 and then temporarily stop the supply of energy automatically.

Next, functions of the treatment system 10 according to this embodiment are described. Described here is the function to inhibit the influence of clamping on the living tissues L1 and L2 when the living tissues L1 and L2 are clamped between the first and second clamp portions 66 and 68. Described thereafter is the function to seal and cut the living tissues L1 and L2 at the same time when energy is applied to the living tissues L1 and L2 clamped between the first and second clamp portions 66 and 68.

A user brings the treatment portion 52 closer to the treatment target living tissues L1 and L2 in a state where the operation portion 44 of the treatment instrument 12 is suitably clamped. The user then suitably operates the open/close lever 46 to relatively open the first and second jaws 62 and 64 (the first and second treatment pieces 52a and 52b) and then disposes the living tissues L1 and L2 between the clamp surfaces 66a and 68a of the first and second clamp portions 66 and 68. In this state, the user operates the open/close lever 46 to grasp the living tissues L1 and L2 between the clamp surfaces 66*a* and 68*a* as shown in FIG. 7A.

In this instance, the treatment body 70 is protruding as much as the first protrusion amount P1 (see FIG. 4B) from the clamp surface 66*a* of the first clamp portion 66. However, the first protrusion amount P1 causes the treatment body 70 to be flush with (i.e., zero protrusion amount) or hardly protrude from the first clamp surface 66*a*, so that an influence on the living tissues L1 and L2 is prevented. Thus, even if the clamp surfaces 66*a* and 68*a* of the first and second clamp portions 66 and 68 are opened relative to each other after the living tissues L1 and L2 have been clamped, the influence on the living tissues L1 and L2 clamped by the treatment body 70 is minimized.

The user again operates the open/close lever 46 to grasp the treatment target living tissues L1 and L2 between the clamp surfaces 66*a* and 68*a* of the first and second clamp portions 66 and 68. The user presses the pedal 16*a* of the foot switch 16 in a state where a desired position to be treated in the living tissues L1 and L2 is clamped. Thus, energy is output to the heating element 72 from the heating element drive circuit 24, and the heating element 72 is heated accordingly. The heating element 72 is controlled so that the treatment surface 70*b* (clamp surface) of the treatment body 70 is raised to a temperature of about 250° C., for example, within a time t1 (e.g., any time of several seconds to several ten seconds) and this temperature is maintained.

The heat energy of the heating element 72 is transmitted to the treatment body 70 from the heat transmission surface 70*a*, and also transmitted to the first clamp portion 66 that forms the depression 67. The first clamp portion 66 is made of a material having a low thermal expansion coefficient, and therefore hardly expands or is difficult to expand. In contrast, the treatment body 70 is made of a material having a high thermal expansion coefficient, and therefore expands. In this instance, the treatment body 70 expands to push the buffer portion 74 aside. The treatment body 70 then protrudes from the clamp surface 66*a* to reach the second protrusion amount P2 greater than the first protrusion amount P1 due to heat transmission from the heating element 72.

If the heating element 72 is heated, the clamp surface 66*a* of the first clamp portion 66 and the treatment surface 70*b* of the treatment body 70 rise to a temperature of about 150° C. to 300° C. within several seconds. Thus, heat energy is applied to the living tissues L1 and L2 so that the living tissues L1 and L2 are sealed with the clamp surface 66*a* of the first clamp portion 66. Heat energy is also applied to the living tissues L1 and L2 by the treatment body 70. In this instance, as shown in FIG. 7B, the treatment body 70 expands, so that the treatment surface 70*b* of the treatment body 70 increases pressure on the living tissues linearly along the longitudinal direction Y. The treatment surface 70*b* of the treatment body 70 increases pressure that operates toward the clamp surface 68*a* of the second clamp portion 68. Thus, positions of the living tissues L1 and L2 that are linearly pressed by the treatment surface 70*b* of the treatment body 70 are lineally cut open. That is, the treatment body 70 cuts open the living tissues L1 and L2 with the treatment surface 70*b* in cooperation with the action of the heat energy when reaching the second protrusion amount P2 from the first protrusion amount P1 in response to the supply of the heat energy.

If a part of the second treatment piece 52*b* that receives the treatment surface 70*b* of the treatment body 70 is rigid, a clearance may be formed between the treatment surface 70*b* and the rigid receiving portion. Due to this clearance, the living tissues L1 and L2 might have parts that are left uncut when the living tissues L1 and L2 are to be cut open. If the treatment surface 70*b* of the treatment body 70 is received by the rigid receiving portion of the second treatment piece 52*b*, the treatment surface 70*b* of the treatment body 70 might receive a load.

Here, at least part of the treatment surface 70*b* of the treatment body 70 abuts on the elastic member 76 disposed in the clamp surface 68*a* of the second clamp portion 68 when the living tissues L1 and L2 are cut open. A clearance is not easily formed between the treatment surface 70*b* of the treatment body 70 and the elastic member 76 owing to the elastic deformation of the elastic member 76. Therefore, the presence of the elastic member 76 can prevent the living tissues from having parts that are left uncut as much as possible. The elastic member 76 has heat resistance and elasticity, and therefore absorbs force resulting from the abutment. Thus, the elastic member 76 can prevent a load on the treatment surface 70*b* of the treatment body 70.

The living tissues L1 and L2 are not uniform in thickness. Thus, force may be applied to the elastic member 76 provided in the clamp surface 68*a* of the second clamp portion 68 from the treatment surface 70*b* of the treatment body 70 from a direction deviating from the Z-direction. In this instance, the elastic member 76 prevents excessive force from being applied to the second clamp portion 68 and the second jaw 64 as much as possible.

As described above, the following can be said according to the treatment system 10 and the treatment instrument 12 in this embodiment.

In this embodiment, the treatment body 70 that is used is several ten times higher in thermal expansion coefficient than the first clamp portion 66. In a state where heat energy is not applied to each of the first clamp portion 66 and the treatment body 70 from the heating element 72, the protrusion amount P1 is at such a degree that the treatment surface 70*b* of the treatment body 70 is flush with or slightly protrudes from the clamp surface 66*a*. Thus, when the living tissues are clamped between the clamp surface 66*a* of the first clamp portion 66 as well as the treatment surface 70*b* of the treatment body 70 and the clamp surface 68*a* of the second clamp portion 68 as well as the elastic member 76, it is possible to prevent a load from being applied to the living tissues especially at the central position of the clamp surface 66*a* of the first clamp portion 66 in the width direction X.

In a state where heat energy is applied to each of the first clamp portion 66 and the treatment body 70 from the heating element 72, the clamp surface 66*a* of the first clamp portion 66 and the treatment surface 70*b* of the treatment body 70 can be raised to a temperature of, for example, about 150° C. to 300° C., and the living tissues can be further pressed by the linear treatment surface 70*b* of the treatment body 70. Thus, the living tissues can be sealed in a region between the clamp surfaces 66*a* and 68*a* of the first and second clamp portions 66 and 68, and the living tissues can be cut open by the treatment surface 70*b* of the treatment body 70 disposed substantially in the center of the clamp surface 66*a* of the first clamp portion 66 in the width direction X. That is, the treatment instrument 12 according to this embodiment can treat the part around the cut position of the living tissues L1 and L2 in a sealed state. Therefore, according to the treatment instrument 12 and the treatment system 10 in this embodiment, the influence of clamping on the living tissues L1 and L2 can be minimized when the living tissues L1 and L2 are clamped between the pair of clamp surfaces 66*a* and 68*a* without the application of energy. According to the treatment instrument 12 and the treatment system 10, when the treatment target living tissues are treated by the application of energy, the treatment body 70 is expanded to increase the protrusion amount of the treatment surface 70b from the clamp surface 66a so that the living tissues L1 and L2 can be treated while higher pressure is applied to some parts of the treatment target living tissues L1 and L2 than to the other parts thereof.

In the treatment instrument 12 according to this embodiment, the elastic member 76 is disposed to receive the treatment surface 70b of the treatment body 70 in the second clamp portion 68. The elastic member 76 has enough heat resistance to a temperature of about 300° C. Thus, when the living tissues L1 and L2 are pressed by the treatment surface 70b of the treatment body 70, a clearance is not easily formed between the treatment surface 70b of the treatment body 70 and the elastic member 76 owing to the elastic defamation of the elastic member 76. Therefore, according to the treatment instrument 12 in this embodiment, the presence of the elastic member 76 can prevent the living tissues L1 and L2 from having parts that are left uncut as much as possible.

In the example described in this embodiment, the heating element 72 is disposed in the first clamp portion 66. It is also appropriate that the heating element 72 be disposed in the first clamp portion 66 and a heating element (not shown) which is heated simultaneously with the heating element 72 be disposed in the second clamp portion 68.

Although the insertion portion 42 includes the treatment portion 52 and the shaft 54 in the example described in this embodiment, the shaft 54 is not necessarily required. It is also appropriate that the treatment portion 52 be directly attached to the operation portion 44.

Next, a first modification of the first embodiment is described with reference to FIG. 8A and FIG. 8B.

As shown in FIG. 8A and FIG. 8B, in this embodiment, the treatment body 70 includes first and second blades 82 and 84. The first and second blades 82 and 84 are made of metallic materials or heat-resistant resin materials different from each other in thermal expansion coefficient. In this embodiment, the first and second blades 82 and 84 are adjacent in the width direction X. In this instance, the first and second blades 82 and 84 may be in or out of contact with each other.

In FIG. 8A, the first protrusion amount (initial protrusion amount) P1 of the first and second blades 82 and 84 is formed to be greater than that of the treatment body 70 shown in FIG. 7A described in the first embodiment. The first protrusion amount P1 can be set suitably for the treatment target living tissues L1 and L2.

For example, an aluminum alloy (thermal expansion coefficient: $23.1 \times E^{-6}[1/K]$) is used for the first blade 82. For example, an Fe—Ni 36% alloy material (thermal expansion coefficient: $0.8 \times E^{-6}[1/K]$) is used for the second blade 84. That is, the thermal expansion coefficients of the first blade 82 and the second blade 84 differ by about 20 times to 30 times. Thus, when the heating element 72 is heated and the heat is transmitted to the first and second blades 82 and 84, the first blade 82 expands more than the second blade 84. The second blade 84 hardly expands. That is, the treatment body 70 includes the first blade (thermal expansion member) 82 by which a treatment surface 86a reaches the second protrusion amount P2 from the first protrusion amount P1 due to the supply of heat energy, and the second blade (protruding body) 84 which is adjacent to the first blade 82 and which includes a treatment surface (a support surface of the living tissues) 86b that protrudes as much as the first protrusion amount P1 from the clamp surface 66a.

The first and second blade 82 and 84 cooperate with each other to form a treatment surface 86. The treatment surface 86 includes the first treatment surface 86a formed in the first blade 82, and the second treatment surface 86b formed in the second blade 84.

Next, functions of the treatment system 10 according to the first modification of the first embodiment are briefly described.

In a state where no energy is supplied to the heating element 72 or the supply of heat energy is stopped, the living tissues L1 and L2 are clamped between the clamp surfaces 66a and 68a of the clamp portions 66 and 68 as shown in FIG. 8A. In this instance, the distance from the clamp surface 66a of the first clamp portion 66 to the treatment surfaces 86a and 86b of the treatment body 70, that is, the first protrusion amount P1 is substantially the same.

The treatment portion 52 shown in FIG. 8A is greater than the treatment portion 52 shown in FIG. 7A in the protrusion amount P1 of the treatment body 70 from the clamp surface 66a of the first clamp portion 66. However, depending on the treatment target living tissues L1 and L2, the influence of the increase of the protrusion amount P1 of the treatment body 70 from the clamp surface 66a of the first clamp portion 66 can be neglected.

Energy is supplied to the heating element 72 of the treatment portion 52 shown in FIG. 8A from the heating element drive circuit 24 (see FIG. 2) to heat the heating element 72 to a suitable temperature (e.g., about 250° C.). The heat of the heating element 72 is transmitted to the first blade 82, the second blade 84, and the clamp surface 66a of the first clamp portion 66.

Thus, the living tissues L1 and L2 which are in contact with the first blade 82, the second blade 84, and the clamp surface 66a of the first clamp portion 66 and which are clamped between the above components and the clamp surface 68a of the second clamp portion 68 are heated and sealed.

In this instance, as shown in FIG. 8B, the first blade 82 expands, so that the treatment surface 86a of the first blade 82 increases pressure on the living tissues L1 and L2 linearly along the longitudinal direction Y. Thus, the positions of the living tissues L1 and L2 that are linearly pressed by the treatment surface 86a of the first blade 82 are lineally cut open.

As described above, the following can be said according to the treatment system 10 and the treatment instrument 12 in this modification.

When the living tissues L1 and L2 are clamped between the clamp surface 66a of the first clamp portion 66 as well as the treatment surface 70b of the treatment body 70 and the clamp surface 68a of the second clamp portion 68 as well as the elastic member 76, it is possible to prevent a load from being applied to the living tissues L1 and L2 at the central position of the clamp surface 66a of the first clamp portion 66 in the width direction X depending on the kinds of living tissues L1 and L2 (e.g., the kinds of organs such as the stomach or liver). Thus, depending on the kinds of living tissues L1 and L2, the application of a load to the living tissues L1 and L2 by clamping can be prevented even by use of the treatment portion 52 according to this modification.

In this modification, when the heating element 72 is heated, the contact area of the part in which the expansion coefficient resulting from the heat to the living tissues L1 and L2 is increased can be larger than in the state shown in FIG. 7A and FIG. 7B, so that press force on the living tissues L1 and L2 can be increased. Thus, as shown in FIG. 8B, when the living tissues L1 and L2 are treated as shown in FIG. 8B, the living tissues L1 and L2 can be cut open at a lower temperature than in the state shown in FIG. 7B.

Therefore, according to the treatment instrument 12 and the treatment system 10 in this embodiment, the influence of clamping on the living tissues L1 and L2 can be minimized when the living tissues L1 and L2 are clamped between the pair of clamp surfaces 66a and 68a without the application of energy. According to the treatment instrument 12 and the treatment system 10, when the treatment target living tissues L1 and L2 are treated by the application of energy, the first blade 82 of the treatment body 70 is expanded to increase the protrusion amount of the treatment surface 86a from the clamp surface 66a so that the living tissues L1 and L2 can be treated while higher pressure is applied to some parts of the treatment target living tissues L1 and L2 than to the other parts thereof.

As shown in FIG. 8A, in this modification, the first protrusion amount P1 of the treatment surface 86 of the treatment body 70 is greater than in the state shown in FIG. 7A. However, it should be understood that the first protrusion amount P1 of the treatment surface 86 of the treatment body 70 may be formed to be similar to the protrusion amount in the state shown in FIG. 7A depending on the treatment target (the kinds of living tissues L1 and L2).

Next, a second modification of the first embodiment is described with reference to FIG. 9A and FIG. 9B. This modification is a further modification of the first modification.

Figure 9A:
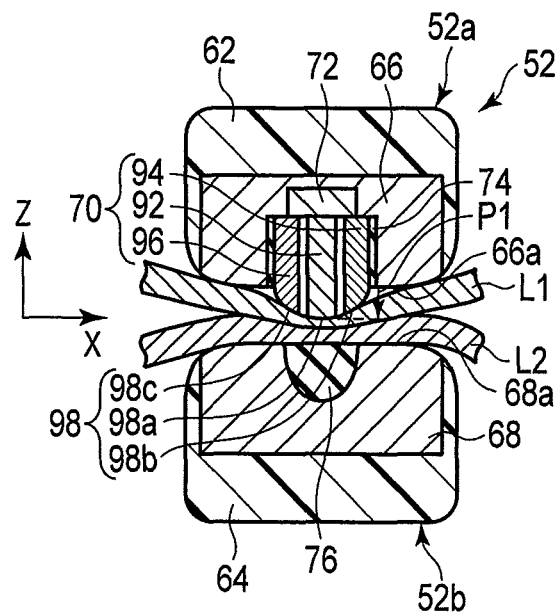
FIG. 9A is a schematic cross sectional view showing the treatment portion of the treatment instrument of the treatment system according to a second modification of the first embodiment, and showing a state where the living tissues are clamped between a thermal expansion member which is disposed between a pair of protruding bodies and a protruding body of the treatment body of the first treatment piece, and the second clamp surface of the second treatment piece.
Figure 9B:
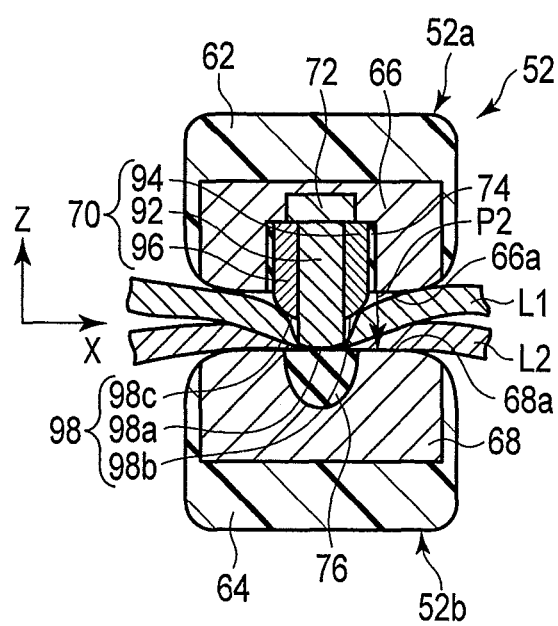
FIG. 9B is a schematic cross sectional view showing the treatment portion of the treatment instrument of the treatment system according to the second modification of the first embodiment, and showing a state where heat energy is applied to the thermal expansion member of the treatment body of the first treatment piece to expand the thermal expansion member, and the living tissues clamped between the second clamp surface of the second treatment piece and the thermal expansion member are cut open by the thermal expansion member.

As shown in FIG. 9A and FIG. 9B, in this embodiment, the treatment body 70 includes a central first blade (thermal expansion member) 92, and second and third blades (protruding bodies) 94 and 96 adjacent to both sides of the first blade 92. The first blade 92 and the second and third blades 94 and 96 are made of metallic materials or heat-resistant resin materials different from each other in thermal expansion coefficient. In this embodiment, the first blade 92 is substantially in the center (on the reference sign C (see FIG. 3)) in the width direction X. The second and third blades 94 and 96 are adjacent to the first blade 92. In this instance, the second blade 94 may be in contact with or away from the first blade 92. Similarly, the third blade 96 may be in contact with or away from the first blade 92.

For example, an aluminum alloy (thermal expansion coefficient: $23.1 \times E^{-6}[1/K]$) is used for the first blade 92. For example, an Fe—Ni 36% alloy material (thermal expansion coefficient: $0.8 \times E^{-6}[1/K]$) is used for the second and third blades 94 and 96. That is, the thermal expansion coefficients of the first blade 92 and the second and third blades 94 and 96 differ by about 20 times to 30 times. Thus, when the heating element 72 is heated and the heat is transmitted to the first to third blades 92, 94, and 96, the first blade 92 expands more than the second and third blades 94 and 96. The second and third blades 94 and 96 hardly expand.

The first to third blades 92, 94, and 96 cooperate with one another to form a treatment surface 98. The treatment surface 98 includes a first treatment surface 98a formed in the first blade 92, a second treatment surface (a support surface of the living tissues) 98b formed in the second blade 94, and a third treatment surface (a support surface of the living tissues) 98c formed in the third blade 96.

According to the treatment instrument 12 and the treatment system 10 in this embodiment, as shown in FIG. 9A, the influence of clamping on the living tissues L1 and L2 can be minimized when the living tissues L1 and L2 are clamped between the pair of clamp surfaces 66a and 68a without the application of energy. According to the treatment instrument 12 and the treatment system 10, as shown in FIG. 9B, when the treatment target living tissues L1 and L2 are treated by the application of energy, the first blade 92 of the treatment body 70 is expanded to increase the protrusion amount of the first treatment surface 98a from the clamp surface 66a so that the living tissues L1 and L2 can be treated while higher pressure is applied to some parts of the treatment target living tissues L1 and L2 than to the other parts thereof.

Next, a third modification of the first embodiment is described with reference to FIG. 10A and FIG. 10B. Here, a further modification of the second modification of the treatment portion 52 shown in FIG. 9A and FIG. 9B is described.

As shown in FIG. 10A and FIG. 10B, in this embodiment, the treatment body 70 includes a central first blade (movable member) 102, second and third blades 104 and 106 adjacent to both sides of the first blade 102, and a shape memory alloy (deformable member) 108. The treatment body 70 according to this embodiment includes the deformable member 108 which is deformed by the supply of heat energy, and the first blade (movable member) 102 which moves in a direction substantially perpendicular to the first clamp surface 66a in response to the deformation of the deformable member 108.

It is preferable that the first blade 102 and the second blade 104 slidably contact each other and that the first blade 102 and the third blade 106 slidably contact each other. The first to third blades 102, 104, and 106 cooperate with one another to form a treatment surface 110. The treatment surface 110 includes a first treatment surface 110a formed in the first blade 102, a second treatment surface 110b formed in the second blade 104, and a third treatment surface 110c formed in the third blade 106.

Here, the same material having a low thermal expansion coefficient can be used for the first to third blades 102, 104, and 106. For example, an Fe—Ni 36% alloy material (thermal expansion coefficient: $0.8 \times E^{-6}[1/K]$) is used for the first to third blades 102, 104, and 106. It is also appropriate to use the same material as that of the first clamp portion 66 for the first to third blades 102, 104, and 106.

The deformable member 108 is disposed between the first blade 102 and the heating element 72. Here, for example, more than one shape memory alloy 108 formed into coil springs are arranged at suitable intervals along the longitudinal direction Y. Each of the shape memory alloys 108 formed into the coil springs memorizes the shape to extend when heated to a suitable temperature higher than the room temperature.

For example, a Ti—Ni alloy is used for the shape memory alloy 108 in this modification. The shape memory alloy 108 can be adjusted to shown its properties to be restored to the memorized shape when heated to a suitable temperature (e.g. about 90° C.).

Thus, if the heating element 72 is heated as has been described in the second modification, the shape memory alloy 108 is heated and then deformed into the state shown in FIG. 10B from the state shown in FIG. 10A. In this instance, the first blade (movable member) 102 moves to a state in which the first blade 102 protrudes as much as the second protrusion amount P2 from the first clamp surface 66a as shown in FIG. 10B from a state in which the first blade 102 protrudes as much as the first protrusion amount P1 from the first clamp surface 66a as shown in FIG. 10A. Therefore, if the heating element 72 is heated, the shape memory alloy 108 is heated so that the first blade 102 can be moved away from the heating element 72.

Even when the shape memory alloy 108 has brought the first blade 102 away from the heating element 72, heat can be transmitted to the first treatment surface 110a of the first blade 102 through the second and third blades 104 and 106.

According to the treatment instrument 12 and the treatment system 10 in this embodiment, the influence of clamping on the living tissues L1 and L2 can be minimized when the living tissues L1 and L2 are clamped between the pair of clamp surfaces 66a and 68a. According to the treatment instrument 12 and the treatment system 10, when the treatment target living tissues L1 and L2 are treated by the application of energy, the first blade 102 of the treatment body 70 is moved by the shape memory alloy 108 to increase the protrusion amount of the first treatment surface 110a from the clamp surface 66a so that the living tissues can be treated while higher pressure is applied to some parts of the treatment target living tissues L1 and L2 than to the other parts thereof.

Instead of the Ti—Ni alloy, a high-temperature shape memory alloy which is deformed into a memorized shape when reaching a temperature of more than 100° C. can also be used for the shape memory alloy 108.

The treatment portion 52 in this modification has been described as the further modification of the treatment portion 52 in the second modification. It is also appropriate to dispose the shape memory alloy 108 between the heat transmission surface 70a of the treatment body 70 of the treatment portion 52 shown in FIG. 7A and FIG. 7B and the heating element 72. Similarly, it is also appropriate to dispose the shape memory alloy 108 between the first blade 82 of the treatment body 70 of the treatment portion 52 shown in FIG. 8A and FIG. 8B and the heating element 72.

In the example described in this embodiment, the shape memory alloy 108 is used between the first blade 102 and the heating element 72. It is also appropriate to use an unshown known bimetal (deformable member) instead of or together with the shape memory alloy 108. The bimetal is a material in which two kinds of metallic materials are bonded to each other. The bimetal can be deformed by use of the difference of thermal expansion coefficients when suitably heated, and can be restored to the original state again when the temperature drops.

As shown in FIG. 10A and FIG. 10B, the elastic member 76 does not necessarily need to be provided in the second clamp portion 68.

Next, a fourth modification of the first embodiment is described with reference to FIG. 11A and FIG. 11B. Here, a further modification of the first embodiment and the first to third modifications is described. The structure of the first jaw 62 described in this modification can be suitably used in the structure of the first jaw 62 described in the first embodiment and the first to third modifications.

As shown in FIG. 11A and FIG. 11B, in this modification, the first treatment piece 52a of the treatment portion 52 includes the first jaw 62 in which the first clamp portion 66 is provided and which can bring the first clamp surface 66a and the second clamp surface 68a closer to and away from each other.

The first jaw 62 includes a support member 162a and an outer cover (heat insulating cover) 162b. Here, a heat-resistant inner cover 162c is provided between the support member 162a and the first clamp portion 66, that is, in the back surface 66b of the first clamp portion 66. The inner cover 162c serves as a spacer which separates the support member 162a from the heating element 72, and does not allow the heat of the heating element 72 to be easily transmitted to the support member 162a, so that the transmission of heat to the outside of the outer cover 162b through the support member 162a is prevented. The inner cover 162c preferably has electric insulation to prevent electric energy from moving between the first clamp portion 66 and/or the heating element 72 and the support member 162a of the first jaw 62. Preferably, the outer cover 162b as well as the inner cover 162c also has electric insulation.

The inner cover 162c is preferably made of a ceramic material or a heat-resistant plastic material. It is also preferable that the inner cover 162c is integrated with the back surface 66b of the first clamp portion 66 by coating.

Here, the inner cover 162c covers the side surface as well as the back surface 66b of the first clamp portion 66. It is also preferable that the side surface of the first clamp portion 66 is formed to be protected not by the inner cover 162c but by the outer cover 162b.

The support member 162a is formed to operate by the operation of the open/close lever 46 shown in FIG. 1. The inner cover 162c, the first clamp portion 66, the heating element 72, the treatment body 70, and the buffer portion 74 operate to follow the operation of the support member 162a. Thus, the first clamp surface 66a and the second clamp surface 68a can be brought closer to and away from each other by the operation of the support member 162a.

A highly rigid material such as an aluminum alloy or stainless steel is preferably used for the support member 162a. Thus, the deformation of the whole first jaw 62 is inhibited.

The outer cover 162b is preferably made of a ceramic material or a heat-resistant plastic material. It is also preferable that an air layer is formed between the outer cover 162b and the support member 162a. It is also preferable that the outer cover 162b is integrated with the support member 162a by coating.

The treatment portion 52 is extremely small, and maintaining its strength is difficult. Thus, if the living tissues are grasped with strong force, a load is applied to the first clamp portion 66 and the first clamp portion 66 is deformed so that it may be difficult to suitably treat the living tissues. When the support member 162a made of a highly rigid material is used as in this modification, the shape of the first clamp portion 66 is easily maintained even if the living tissues are grasped with strong force.

The first clamp portion 66 may be fixed to the support member 162a or may be slidable on the support member 162a. That is, it is also preferable that the inner cover 162c, the first clamp portion 66, the heating element 72, the treatment body 70, and the buffer portion 74 are slidable on the support member 162a like a seesaw.

The inner cover 162c is not necessarily required, and the side surface of the first clamp portion 66 can also be protected by the outer cover 162b.

Although the first jaw 62 has the support member 162a, the outer cover 162b, and the inner cover 162c in this modification, it is also appropriate that the second jaw 64 has a similar structure.

Next, the second embodiment is described with reference to FIG. 12 to FIG. 15. This embodiment is a modification of the first embodiment including each of its modifications. The same components as those described in the first embodiment or components having the same functions are denoted by the same reference signs and are not described in detail.

In the example described here, the living tissues L1 and L2 can be joined to each other not only by use of the heating element 72 but also by the discharge of staples 180.

Figure 12:
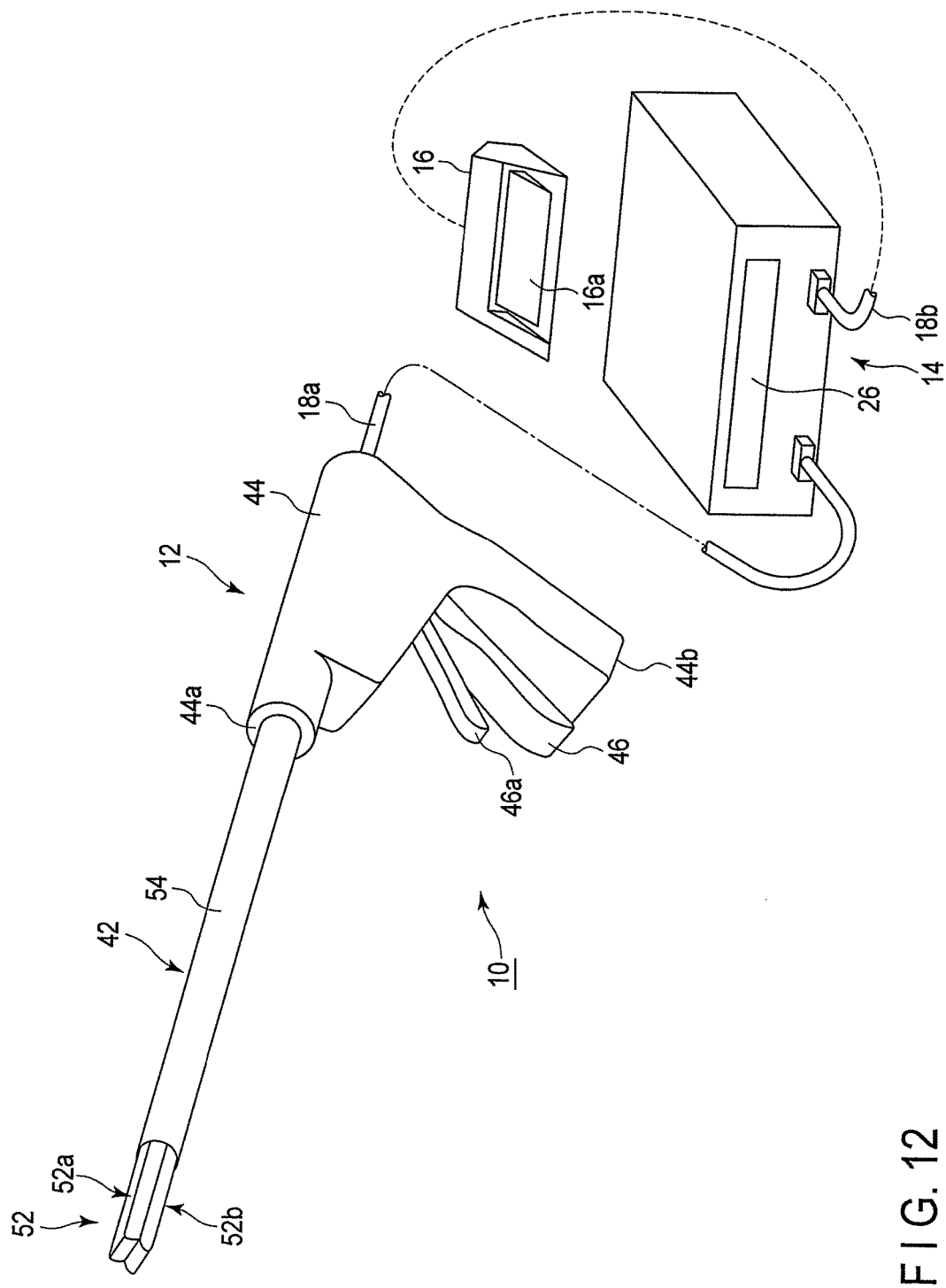
FIG. 12 is a schematic diagram showing the treatment system according to a second embodiment.

As shown in FIG. 12, the operation portion 44 includes a drive lever 46a provided in parallel with the open/close lever 46. The drive lever 46a functions to move a later-described pusher rod 182.

Figure 13:
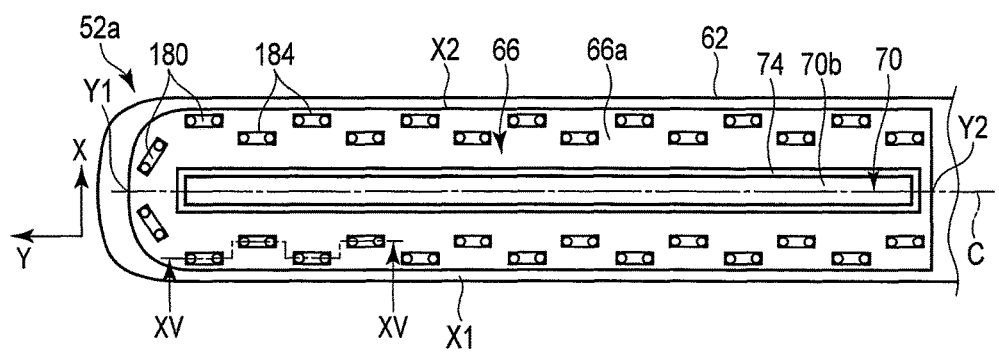
FIG. 13 is a schematic diagram showing the clamp surface in the first clamp portion of the first treatment piece of the treatment portion of the treatment instrument of the treatment system according to the second embodiment.
Figure 14:
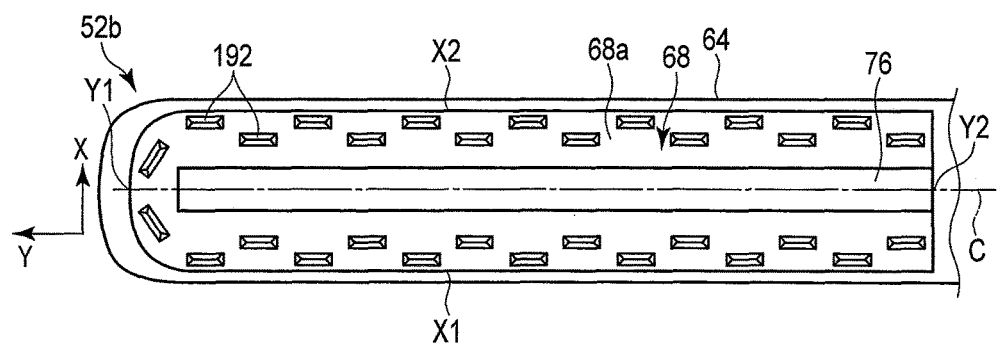
FIG. 14 is a schematic diagram showing a clamp surface in a second clamp portion of a second treatment piece of the treatment portion of the treatment instrument of the treatment system according to the second embodiment.
Figure 15:
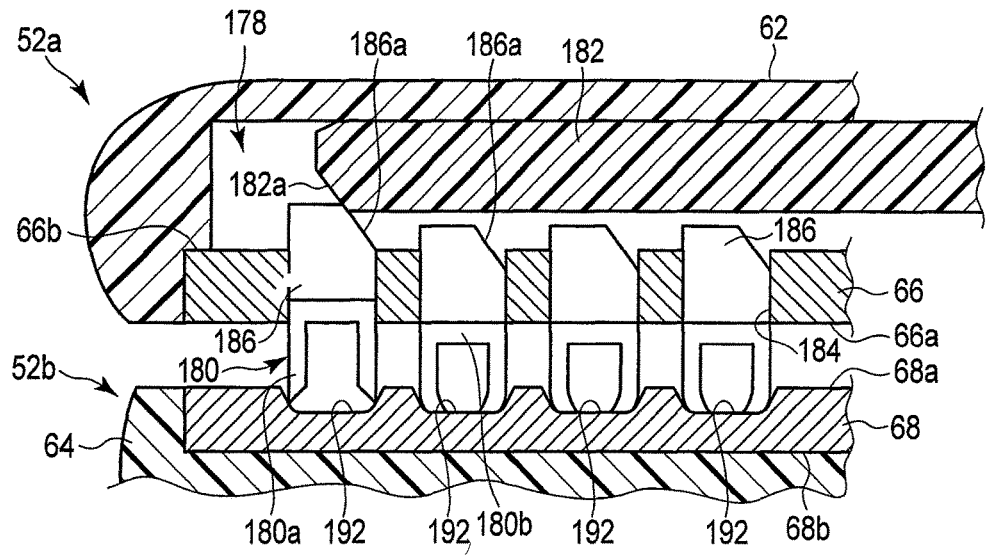
FIG. 15 is a schematic longitudinal sectional view taken along the XV-XV line in FIG. 13 showing a state where substantially U-shaped staples are protruded from the first clamp portion of the treatment portion of the treatment instrument of the treatment system according to the second embodiment so that legs of the staples are folded by the clamp surface in the second clamp portion.

As shown in FIG. 13 to FIG. 15, in this embodiment, the first treatment piece 52a includes the surgical staples 180 which are substantially U-shaped hooks. The surgical staples 180 are preferably made of, for example, a bio-absorbable surgical material.

More than one staple 180 is housed in a magazine 178 between the first jaw 62 and the back surface 66b of the first clamp portion 66.

As shown in FIG. 15, in the magazine 178 of the first jaw 62 to discharge the surgical staples (absorbent materials) 180, the pusher rod 182 having an inclined surface 182a is housed movably parallel to the longitudinal direction Y. The pusher rod 182 according to this embodiment operates in accordance with the operation of the drive lever 46a.

In the magazine 178, the staple 180 having a pair of legs 180a and an arm that connects the legs 180a to each other is housed to be able to protrude the legs 180a toward the clamp surface 68a of the second clamp portion 68. In the clamp surface 66a of the first clamp portion 66, guide slots (discharge openings) 184 are formed to face the pusher rod 182. In each of the guide slots 184, a staple pusher 186 having an inclined surface 186a which is inclined in the same manner as the inclined surface 182a of the pusher rod 182 is provided slidably on the guide slot 184.

As shown in FIG. 14 and FIG. 15, staple deformation slots (clinchers) 192 are formed in the clamp surface 68a of the second clamp portion 68. Each of the staple deformation slots 192 has its bottom surface that is, for example, substantially arc-shaped so that the pair of legs 180a (see FIG. 15) of each of the staples 180 can be folded inward and deformed. Therefore, the clamp surface 68a of the second clamp portion 68 also has a function as an anvil of the staples 180.

Each of the guide slots 184 shown in FIG. 13 and each of the staple deformation slots 192 shown in FIG. 14 are formed at positions to face each other.

Functions of the curative treatment system 10 according to this embodiment are briefly described. The contents described in the first embodiment are therefore not mentioned.

As has been described in the first embodiment, the living tissues are treated by use of heat energy.

If the drive lever 46a is then brought closer to the other end 44b of the operation portion 44, the pusher rod 182 is moved forward by a known mechanism. Accordingly, the pair of legs 180a of the staple 180 pass through the guide slot 184 and pierce the living tissues which have been treated by use of the heat energy. The pair of legs 180a of the staple 180 are folded by the staple deformation slot 192 to face each other so that the staple 180 is fixed to the living tissues.

Although the living tissues L1 and L2 are fixed to each other by the staples 180 after the living tissues are first treated with the heat energy in the case described here, it is also appropriate that the living tissues be treated, for example, cut open by use of heat energy in a state where the living tissues are held by the staples.

Next, the third embodiment is described with reference to FIG. 16. This embodiment is a modification of the first and second embodiments. The same components as those described in the first and second embodiments or components having the same functions are denoted by the same reference signs and are not described in detail.

In the example described in the first embodiment, the heating element 72 is disposed in the first clamp portion 66. It is also appropriate that the first clamp portion 66 and the second clamp portion 68 be formed as electrodes (energy output portions), respectively. It is also appropriate to combine the heat energy by the heating element 72 with high-frequency energy using the first clamp portion 66 and the second clamp portion 68 as the electrodes to treat the living tissues.

Figure 16:
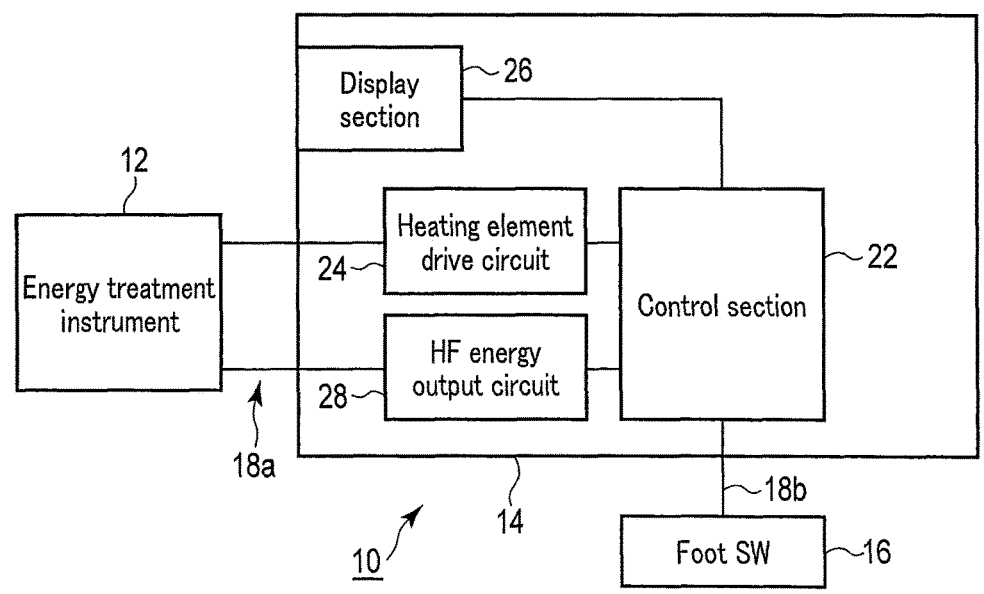
FIG. 16 is a schematic block diagram showing the treatment system according to a third embodiment.

In this case, as shown in FIG. 16, the controller 14 includes a high-frequency energy drive circuit (energy output circuit) 28 as an energy source. The high-frequency energy drive circuit 28 is electrically connected to the first clamp portion (first high-frequency electrode) 66 and the second clamp portion (second high-frequency electrode) 68.

In a state where the living tissues L1 and L2 are grasped between the electrodes, that is, between the first and second clamp portions 66 and 68, energy is output to between the first and second clamp portions 66 and 68 from the high-frequency energy drive circuit 28, and energy is output to between the first and second clamp portions 66 and 68 from the heating element drive circuit 24.

The living tissues between the first and second clamp portions 66 and 68 are dehydrated by Joule heat from high-frequency energy, and heat is transmitted to the clamp surfaces 66a and 68a by heat energy resulting from the heating of the heating element 72 so that the living tissues are treated. In this instance, the treatment body 70 expands due to the heating of the heating element 72, so that gradually increasing pressure can be applied to the living tissues L1 and L2.

The living tissues L1 and L2 between the first and second clamp portions 66 and 68 rise in temperature in a shorter time by the high-frequency energy than by use of heat transmission from the heating element 72 described in the first embodiment. Thus, the treatment instrument 12 according to this embodiment can treat the living tissues L1 and L2, for example, cut open the living tissues L1 and L2 with the treatment surface 70b in a shorter time than the treatment instrument 12 described in the first embodiment. The heating element 72 of the treatment instrument 12 according to this embodiment can complete the treatment at a lower temperature than in the treatment by the treatment instrument 12 described in the first embodiment.

It should be understood that the mechanism that can discharge the staples 180 described in the second embodiment may be combined with the treatment instrument 12 according to this embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A treatment instrument comprising:
a first clamp portion including a first clamp surface;
a second clamp portion including a second clamp surface which faces the first clamp surface and which cooperates with the first clamp surface to clamp a living tissue; and
a treatment body that is provided in the first clamp surface and includes a linear treatment surface (1) extending in a longitudinal direction of the first clamp surface and (2) linearly protruding toward the second clamp surface in response to the supply of heat energy to the treatment body, the linear treatment surface of the treatment body being configured to linearly press and linearly heat the living tissue to linearly cut the living tissue; wherein:
the treatment body (1) protrudes a first protrusion amount from the first clamp surface when the supply of the heat energy is stopped and (2) protrudes a second protrusion amount from the first clamp surface in response to the supply of the heat energy; and
the second protrusion amount is larger than the first protrusion amount.

2. The treatment instrument according to claim 1, wherein the treatment surface of the treatment body is extended along a longitudinal direction of the first clamp portion, and the treatment body is configured to cut the living tissue with the treatment surface in cooperation with the action of the heat energy when the treatment body protrudes toward the second clamp surface in response to the supply of heat energy to reach a predetermined protrusion amount.

3. The treatment instrument according to claim 1, wherein the treatment surface of the treatment body has (1) a length along a longitudinal direction of the first clamp portion and (2) a width shorter than the length of the treatment surface and smaller than the width of the first clamp portion in a width direction that intersects at right angles with the longitudinal direction.

4. The treatment instrument according to claim 1, wherein the treatment body is formed by a thermal expansion member which expands in response to the supply of the heat energy.

5. The treatment instrument according to claim 1, wherein the treatment body includes a deformable member which is deformed by the supply of the heat energy, and a movable member which moves in a direction substantially perpendicular to the first clamp surface in response to the deformation of the deformable member.

6. The treatment instrument according to claim 1, wherein the second clamp surface includes an elastic member which has heat resistance to the temperature of the treatment body that is being supplied with the heat energy and which receives the treatment surface of the treatment body.

7. The treatment instrument according to claim 1, further comprising a jaw in which the first clamp portion is provided and which is configured to bring the first clamp surface and the second clamp surface closer to and away from each other.

8. The treatment instrument according to claim 1, further comprising a jaw in which the second clamp portion is provided and which is configured to bring the first clamp surface and the second clamp surface closer to and away from each other.

9. The treatment instrument according to claim 1, wherein the first clamp portion is configured to transmit, to the first clamp surface, the heat energy that is transmitted to the treatment body.

10. The treatment instrument according to claim 1, wherein:
the first clamp portion is formed as a first high-frequency electrode, and the second clamp portion is formed as a second high-frequency electrode which cooperates with the first high-frequency electrode to treat the living tissue.

11. The treatment instrument according to claim 1, wherein:
the clamp surface of one of the first and second clamp portions includes a discharge opening which is configured to discharge a staple held in the one of the first and second clamp portions, and
the clamp surface of the other of the first and second clamp portions includes a clincher which bends legs of the staple discharged from the discharge opening.

12. A treatment system comprising:
the treatment instrument according to claim 1;
a heating element provided in the first clamp portion of the treatment instrument;
an energy output circuit which is electrically connected to the heating element and which supplies energy to the heating element; and
a control section which controls the energy output circuit.

13. The treatment instrument according to claim 1, comprising a heating element which is provided in the first clamp portion and which is configured to supply the heat energy to the treatment body and to transfer the heat energy to the treatment surface.

14. A treatment instrument comprising:
a first clamp portion including a first clamp surface;
a second clamp portion including a second clamp surface which faces the first clamp surface and which cooperates with the first clamp surface to clamp a living tissue; and
a treatment body that is provided in the first clamp surface and includes:
a linear treatment surface (1) extending in a longitudinal direction of the first clamp surface and (2) linearly protruding toward the second clamp surface in response to the supply of heat energy to the treatment body, the linear treatment surface of the treatment body being configured to linearly press and linearly heat the living tissue to linearly cut the living tissue;
a first protruding body having a support surface which protrudes a first protrusion amount from the first clamp surface and which supports the living tissue, and
a thermal expansion member which is adjacent to the first protruding body and, when heated, protrudes more than the first protrusion amount from the first clamp surface.

15. The treatment instrument according to claim 14, wherein the treatment body further includes a second protruding body which is adjacent to the thermal expansion member at a position opposite to the first protruding body and which includes a support surface that protrudes as much as the first protrusion amount from the first clamp surface and that supports the living tissue.

16. A treatment instrument comprising:
a first clamp portion including a first clamp surface;
a second clamp portion including a second clamp surface which faces the first clamp surface and which cooperates with the first clamp surface to clamp a living tissue; and
a treatment body that is provided in the first clamp surface and includes a linear treatment surface (1) extending in a longitudinal direction of the first clamp surface and (2) linearly protruding toward the second clamp surface in response to the supply of heat energy to the treatment body, the linear treatment surface of the treatment body being configured to linearly press and linearly heat the living tissue to linearly cut the living tissue;
wherein at all points of the linear treatment surface:
a width of the linear treatment surface that intersects at a right angle with the longitudinal direction of the first clamp surface is smaller than a width of the first clamp surface that intersects at a right angle with the longitudinal direction of the first clamp surface, and a length of the linear treatment surface in the longitudinal direction is longer than the width of the first clamp surface that intersects at a right angle with the longitudinal direction of the first clamp surface.

17. The treatment instrument according to claim 16, wherein the first clamp portion includes a pair of outer edges in the longitudinal direction of the first clamp surface, and the treatment body is provided on the center of the pair of outer edges.

18. A treatment instrument comprising:

a first clamp portion including a first clamp surface;

a second clamp portion including a second clamp surface which faces the first clamp surface and which cooperates with the first clamp surface to clamp a living tissue; and a treatment body that is provided in the first clamp surface and includes a linear treatment surface (1) extending in a longitudinal direction of the first clamp surface and (2) linearly protruding toward the second clamp surface in response to the supply of heat energy to the treatment body, the linear treatment surface of the treatment body being configured to linearly press and linearly heat the living tissue to linearly cut the living tissue; wherein:

the first clamp portion includes a depression formed in the first clamp surface along the longitudinal direction and a pair of outer edges in a width direction that intersects at a right angle with the longitudinal direction, the depression is provided between the pair of outer edges and includes a pair of edges along the longitudinal direction, the first clamp surface is provided between one of the pair of edges of the depression and one of the pair of outer edges of the first clamp portion and between a second of the pair of edges of the depression and a second of the pair of outer edges of the first clamp portion, and the treatment body is provided in the depression along the longitudinal direction.

19. The treatment instrument according to claim 18, comprising buffer portions provided between the treatment body and the one of the pair of edges of the depression and between the treatment body and the second of the pair of edges of the depression.

20. A treatment instrument comprising:

a first jaw comprising (1) a first clamp portion having a first clamp surface and (2) a treatment body having a treatment surface; and a second jaw comprising a second clamp portion having a second clamp surface; wherein:

the second clamp surface and a combination of the first clamp surface and the treatment surface face each other and are configured to clamp living tissue therebetween;

the treatment body has a higher thermal expansion coefficient than the first clamp portion; and when the treatment body is heated above a certain temperature, the treatment body will expand more than the first clamp portion such that the treatment surface extends uniformly further towards the second clamp surface than the first clamp surface.

21. The treatment instrument according to claim 20, wherein:

the treatment body is received in a recess formed by the first clamp portion; and the first jaw further comprises an elastically deformable buffer material between the first clamp portion and the treatment body.

22. The treatment instrument according to claim 21, wherein the first jaw further comprises a heating element positioned in the recess formed by the first clamp portion between the treatment body and the first clamp portion.

23. The treatment instrument according to claim 22, wherein the heating element is in contact with the treatment body.

24. The treatment instrument according to claim 23, wherein:

the first jaw has a longitudinal direction;

the heating element and the treatment body extend along the longitudinal direction; and an inner surface of the heating element abuts an outer surface of the treatment body.

25. The treatment instrument according to claim 24, wherein:

the treatment body has side and end surfaces; and the elastically deformable buffer material is between the side and end surfaces of the treatment body and the first clamp portion.

* * * * *